(12) United States Patent
Ortiz et al.

(10) Patent No.: US 8,147,506 B2
(45) Date of Patent: Apr. 3, 2012

(54) METHOD AND CLAMP FOR GASTRIC REDUCTION SURGERY

(75) Inventors: Mark S. Ortiz, Milford, OH (US); William J. Kraimer, Mason, OH (US); Michael J. Stokes, Cincinnati, OH (US); David B. Griffith, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1302 days.

(21) Appl. No.: 11/197,528

(22) Filed: Aug. 5, 2005

(65) Prior Publication Data

US 2007/0032807 A1    Feb. 8, 2007

(51) Int. Cl.
*A61B 17/08* (2006.01)

(52) U.S. Cl. ........................................ 606/151

(58) Field of Classification Search ................ 606/151, 606/157, 158; 600/37; D28/39; 24/67 R, 24/67.3, 67.5, 67.7, 437, 441, 488–490, 493–496, 24/500, 501, 506; 132/277, 279
See application file for complete search history.

(56) References Cited

U.S. PATENT DOCUMENTS

| | | | | |
|---|---|---|---|---|
| 2,622,604 A | * | 12/1952 | Buckner | 132/277 |
| 2,829,654 A | * | 4/1958 | Fay | 132/277 |
| 3,598,125 A | * | 8/1971 | Cogley | 606/158 |
| 5,047,046 A | * | 9/1991 | Bodoia | 606/205 |
| 5,080,663 A | | 1/1992 | Mills et al. | |
| 5,376,101 A | | 12/1994 | Green et al. | |
| 5,437,681 A | | 8/1995 | Meade et al. | |
| 5,462,558 A | | 10/1995 | Kolesa et al. | |
| 5,514,159 A | | 5/1996 | Matula et al. | |
| 5,540,705 A | | 7/1996 | Meade et al. | |
| 5,549,621 A | * | 8/1996 | Bessler et al. | 606/151 |
| 5,571,119 A | | 11/1996 | Atala | |
| 5,709,693 A | | 1/1998 | Taylor | |
| 5,713,910 A | | 2/1998 | Gordon et al. | |
| 5,814,071 A | | 9/1998 | McDevitt et al. | |
| 6,036,694 A | | 3/2000 | Goble et al. | |
| 6,231,561 B1 | * | 5/2001 | Frazier et al. | 604/500 |
| 6,346,111 B1 | | 2/2002 | Gordon et al. | |
| 6,374,463 B1 | * | 4/2002 | Kaufman | 24/67.5 |
| 6,443,962 B1 | | 9/2002 | Gaber | |
| 6,454,778 B2 | | 9/2002 | Kortenbach | |
| 6,494,888 B1 | | 12/2002 | Laufer et al. | |
| 6,506,196 B1 | | 1/2003 | Laufer | |
| D473,342 S | * | 4/2003 | Shyu | D28/40 |
| 6,558,400 B2 | * | 5/2003 | Deem et al. | 606/151 |
| 6,656,194 B1 | | 12/2003 | Gannoe et al. | |
| 6,663,639 B1 | | 12/2003 | Laufer et al. | |
| 6,719,763 B2 | | 4/2004 | Chung et al. | |
| 6,719,764 B1 | | 4/2004 | Gellman et al. | |
| 6,746,460 B2 | | 6/2004 | Gannoe et al. | |
| 6,746,461 B2 | | 6/2004 | Fry | |
| 6,755,843 B2 | | 6/2004 | Chung et al. | |
| 6,773,440 B2 | | 8/2004 | Gannoe et al. | |

(Continued)

FOREIGN PATENT DOCUMENTS

EP     1545336     6/2005

(Continued)

*Primary Examiner* — Gary Jackson
*Assistant Examiner* — L Bachman

(57) ABSTRACT

A method for gastric reduction surgery includes the step of applying at least one clamp to the stomach in a manner forming a gastric pouch. The clamp includes a clamp body shaped and dimensioned to create a gastric pouch with a standard size from approximately 15 cc to approximately 30 cc.

3 Claims, 6 Drawing Sheets

U.S. PATENT DOCUMENTS

| | | |
|---|---|---|
| 6,835,200 B2 | 12/2004 | Laufer et al. |
| 6,869,438 B2 | 3/2005 | Chao |
| 6,908,427 B2 | 6/2005 | Fleener et al. |
| 6,923,819 B2 | 8/2005 | Meade et al. |
| 2002/0107530 A1 | 8/2002 | Sauer et al. |
| 2003/0083674 A1 | 5/2003 | Gibbens, III |
| 2003/0171760 A1 | 9/2003 | Gambale |
| 2003/0181924 A1 | 9/2003 | Yamamoto et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2005/0228504 A1* | 10/2005 | Demarais .................... 623/23.65 |
| 2006/0167474 A1* | 7/2006 | Bloom et al. .................. 606/142 |

FOREIGN PATENT DOCUMENTS

| | | |
|---|---|---|
| EP | 1569709 | 9/2005 |
| WO | WO00/61012 | 10/2000 |
| WO | WO01/10312 | 2/2001 |
| WO | WO01/66001 | 9/2001 |
| WO | WO02/35980 | 5/2002 |
| WO | WO2004087014 | 10/2004 |

* cited by examiner

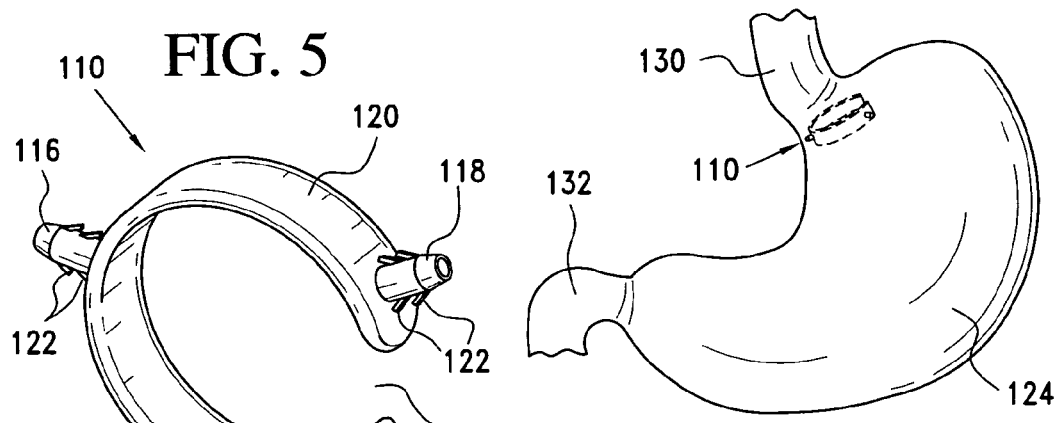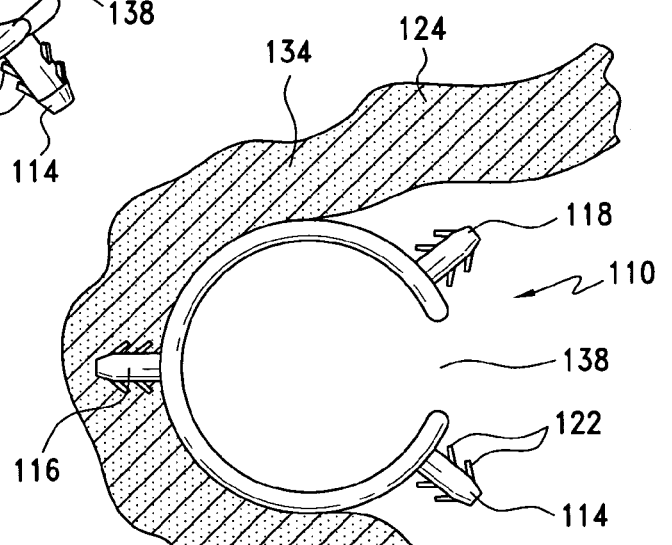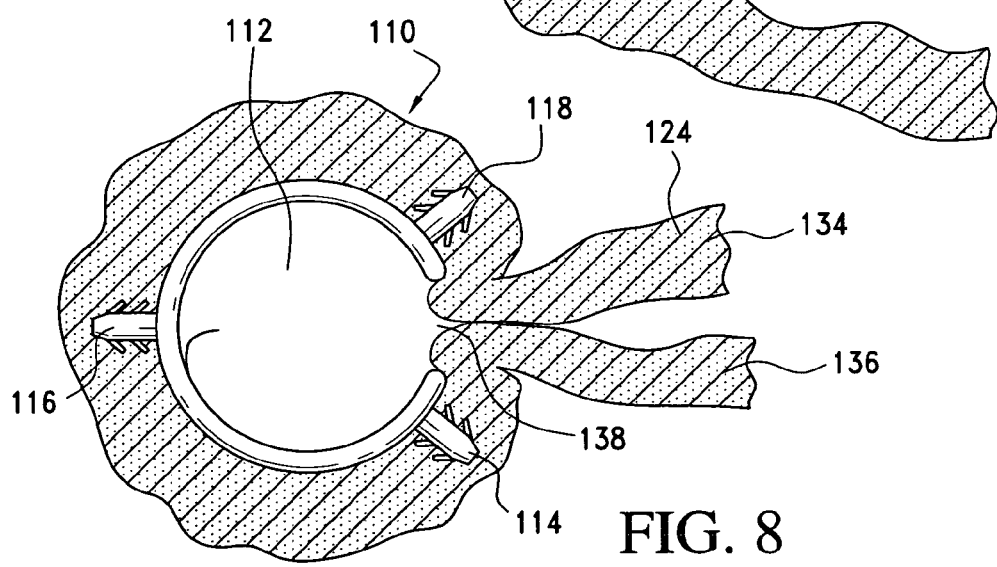

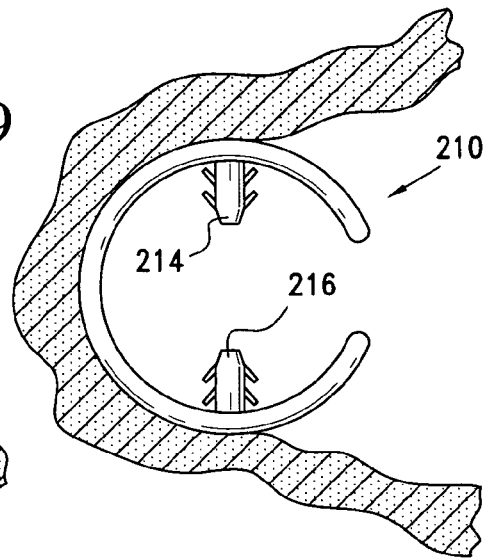
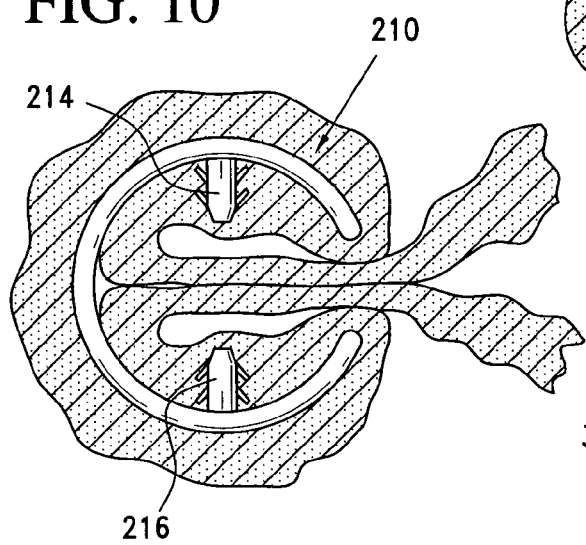
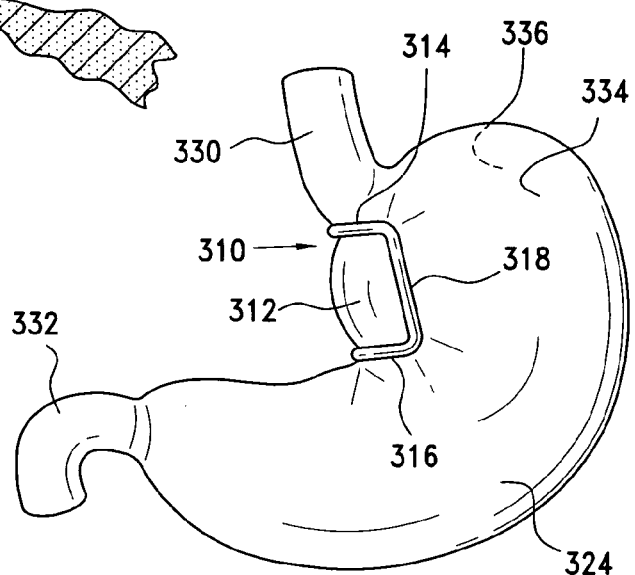
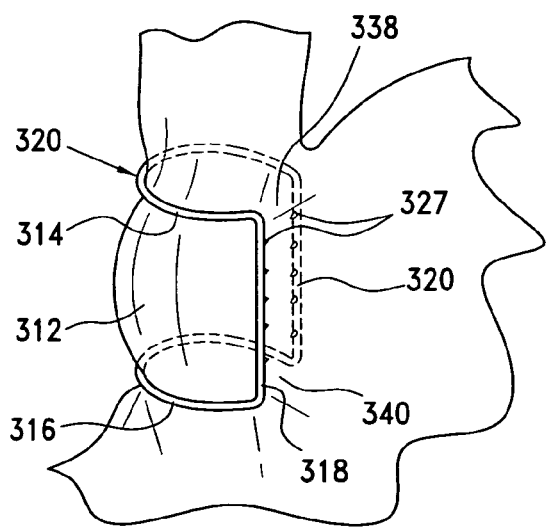

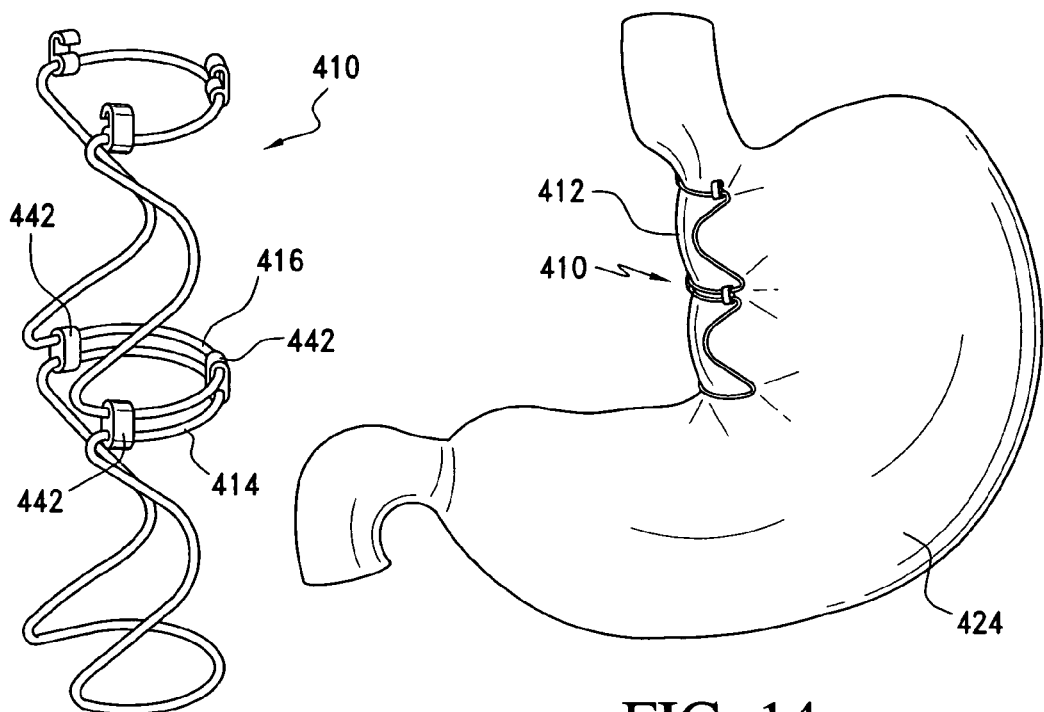
FIG. 13
FIG. 14
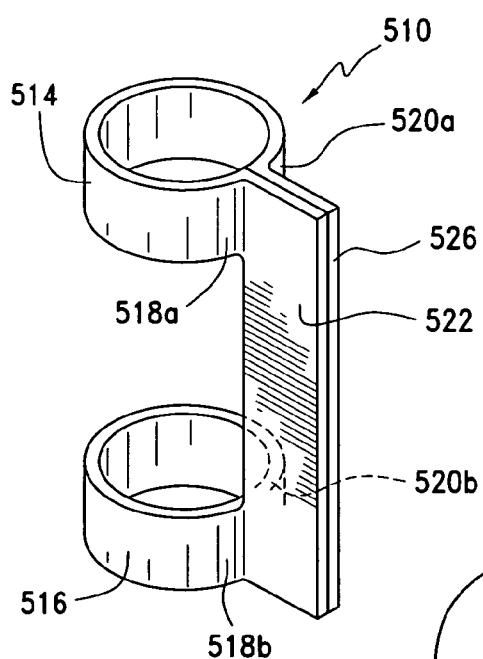
FIG. 15
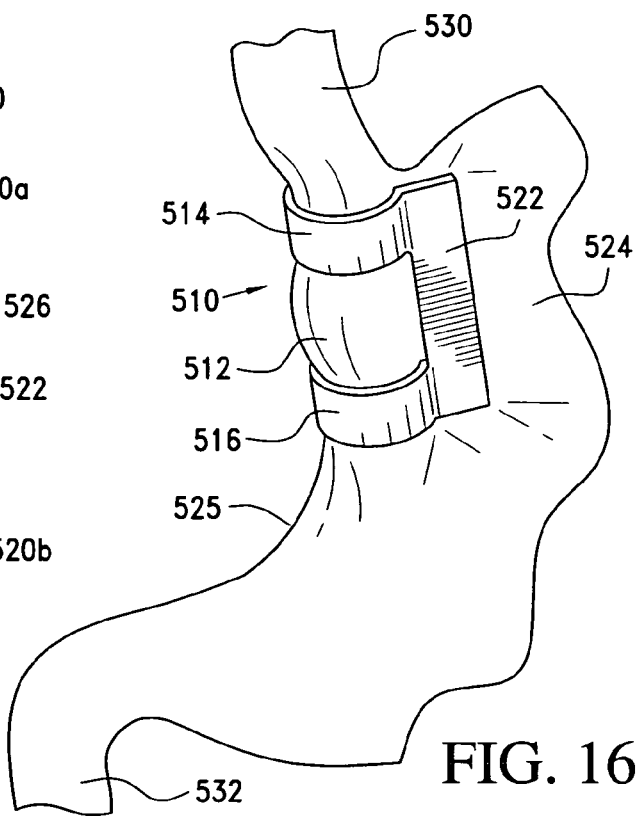
FIG. 16

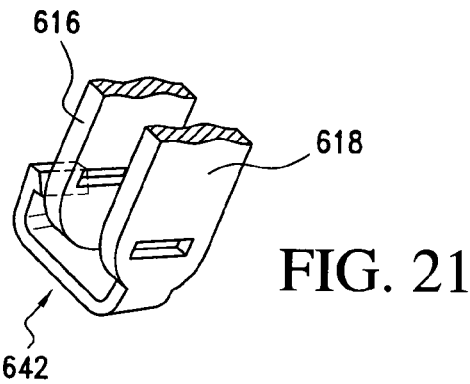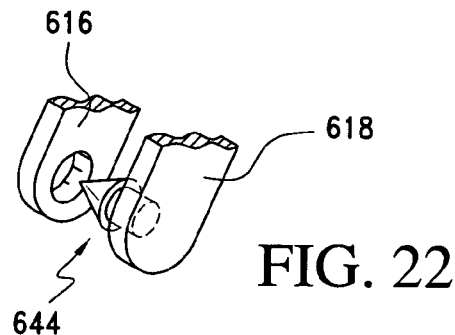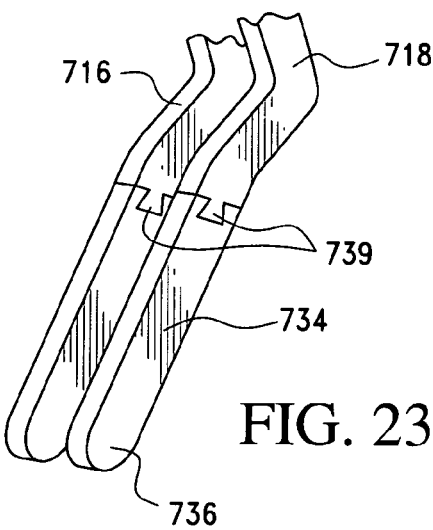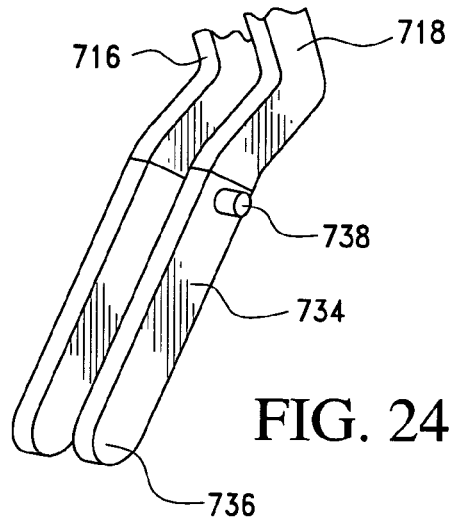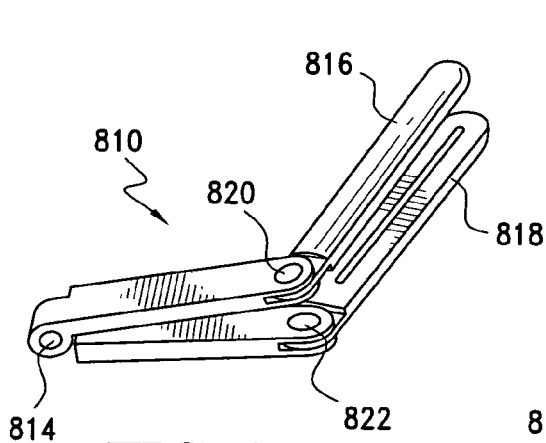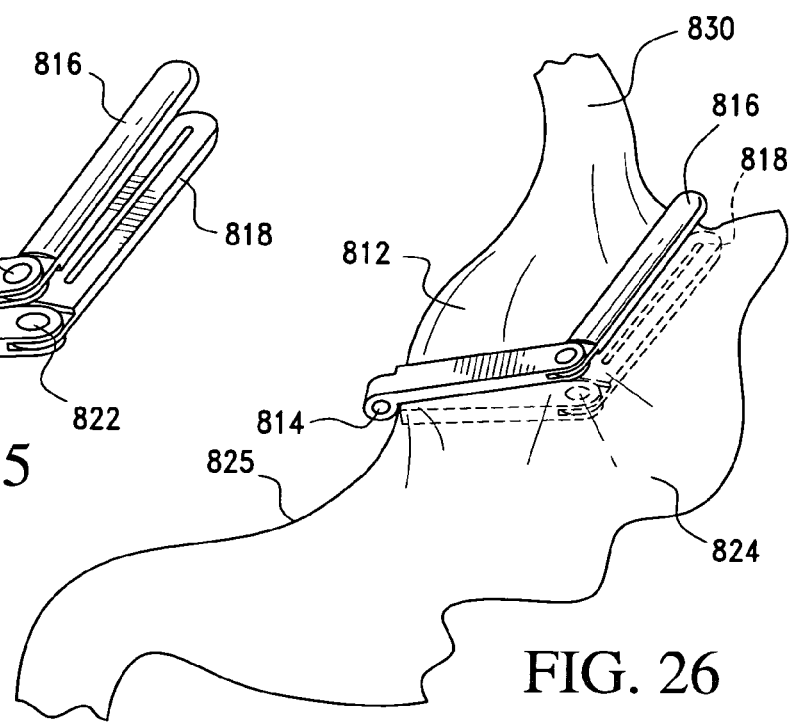

METHOD AND CLAMP FOR GASTRIC REDUCTION SURGERY

BACKGROUND OF THE INVENTION

1. Field of the Invention

The present invention relates to gastric reduction surgery. More particularly, the invention relates to a method and apparatus for performing gastric reduction through the application of a series of clamps.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. Currently, the most commonly performed procedure is Roux-en-Y gastric bypass (RYGB). This operation is highly complex and is commonly utilized to treat people exhibiting morbid obesity. Greater than 100,000 procedures are performed annually in the United States alone. Other forms of bariatric surgery include Fobi pouch, bilio-pancreatic diversion, and gastroplastic or "stomach stapling". In addition, implantable devices are known which limit the passage of food through the stomach and affect satiety.

RYGB involves movement of the jejunum to a high position using a Roux-en-Y loop. The stomach is completely divided into two unequal portions (a smaller upper portion and a larger lower gastric pouch) using an automatic stapling device. The upper pouch typically measures less than about 1 ounce (or 20 cc), while the larger lower pouch remains generally intact and continues to secrete stomach juices flowing through the intestinal track.

A segment of the small intestine is then brought from the lower abdomen and joined with the upper pouch to form an anastomosis created through a half-inch opening, also called the stoma. This segment of the small intestine is called the "Roux loop" and carries the food from the upper pouch to the remainder of the intestines, where the food is digested. The remaining lower pouch, and the attached segment of duodenum, are then reconnected to form another anastomotic connection to the Roux loop at a location approximately 50 to 150 cm from the stoma, typically using a stapling instrument. It is at this connection that the digestive juices from the bypass stomach, pancreas, and liver, enter the jejunum and ileum to aid in the digestion of food. Due to the small size of the upper pouch, patients are forced to eat at a slower rate and are satiated much more quickly. This results in a reduction in caloric intake.

The conventional RYGB procedure requires a great deal of operative time. Because of the degree of invasiveness, postoperative recovery time can be quite lengthy and painful.

In view of the highly invasive nature of the current RYGB procedure, other less invasive procedures have been developed. The most common form of gastric reduction surgery involves the application of vertical staples along the stomach to create an appropriate pouch. This procedure is commonly performed laparoscopically and, as such, requires substantial preoperative, operative, postoperative resources.

In addition to these surgical procedures, gastric bands are commonly employed as a less complex alternative. However, gastric band procedures have complications, for example, erosion of the band through the gastric wall. As a result, their general acceptance within the US marketplace has been limited.

With the foregoing in mind, procedures that allow for the performance of gastric reduction surgery in a time efficient and patient friendly manner are needed. The present invention provides such a method and an associated apparatus.

SUMMARY OF THE INVENTION

It is, therefore, an object of the present invention to provide a method for gastric reduction surgery including the step of applying at least one clamp to the stomach in a manner forming a gastric pouch.

It is also an object of the present invention to provide a clamp for gastric reduction surgery including a clamp body shaped and dimensioned to create a gastric pouch with a standard size from approximately 15 cc to approximately 30 cc.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 5, 6, 7 and 8 disclose an alternate embodiment of a clamp for use in accordance with the present invention.

FIGS. 9 and 10 disclose another embodiment of a clamp for use in accordance with the present invention.

FIGS. 11 and 12 disclose yet another embodiment of a clamp for use in accordance with the present invention.

FIGS. 13 and 14 show a further clamp for use in accordance with the present invention.

FIGS. 15 and 16 disclose still another embodiment of a clamp for use in accordance with the present invention.

FIGS. 17, 18, 19, 20, 21 and 22 show another embodiment of a clamp for use in accordance with the present invention.

FIGS. 23 and 24 disclose another embodiment for a clamp for use in accordance with the present invention.

FIGS. 25 and 26 show yet a further clamp for use in accordance with the present invention.

DESCRIPTION OF THE PREFERRED EMBODIMENTS

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

Figure 1:
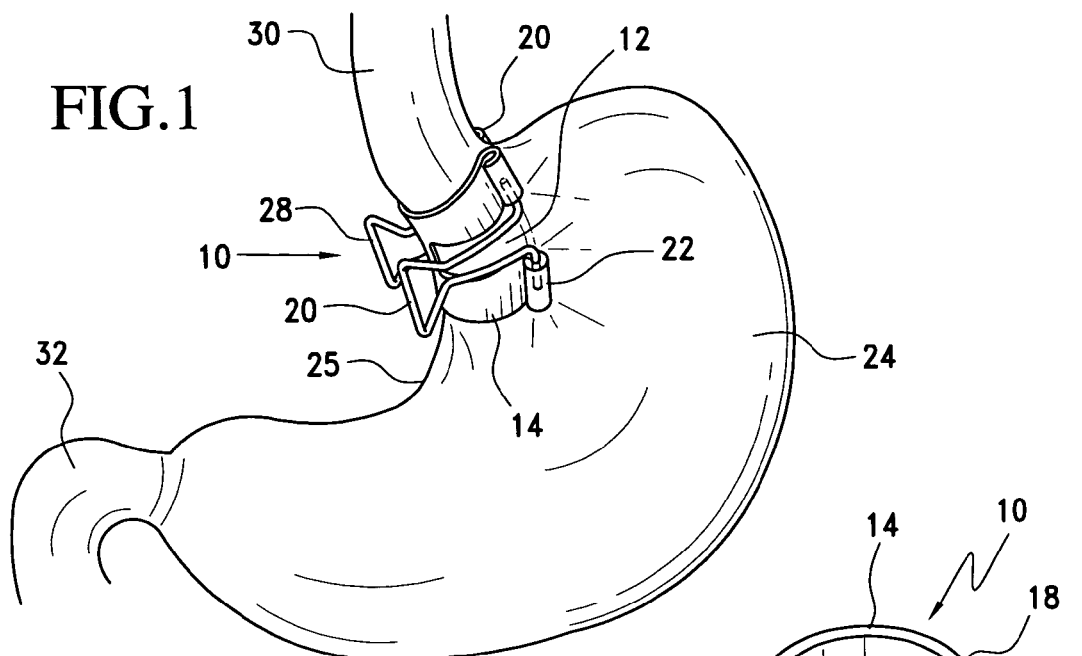
FIGS. 1, 2, 3 and 4 disclose a clamp for use in gastric reduction surgery in accordance with the present invention.
Figure 2:
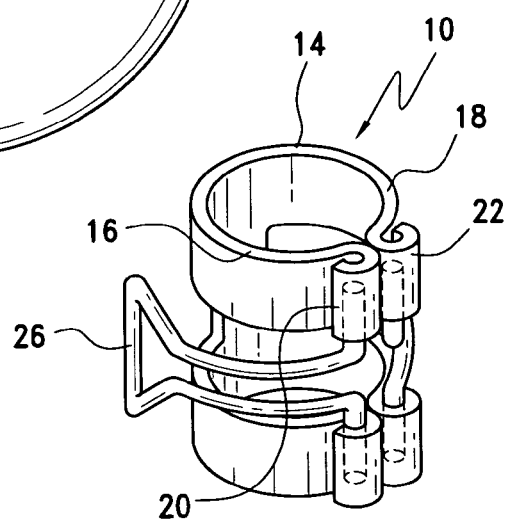
Figure 3:
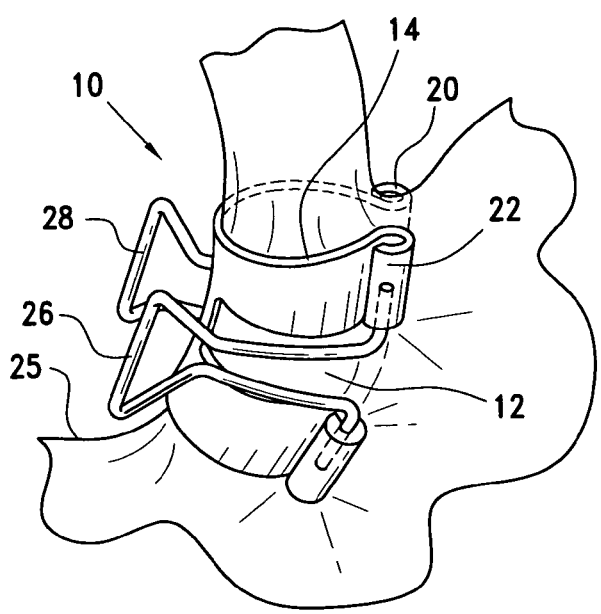
Figure 4:
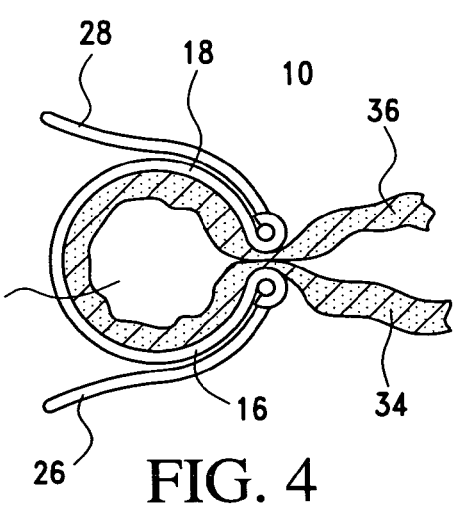
Figures 17, 18:
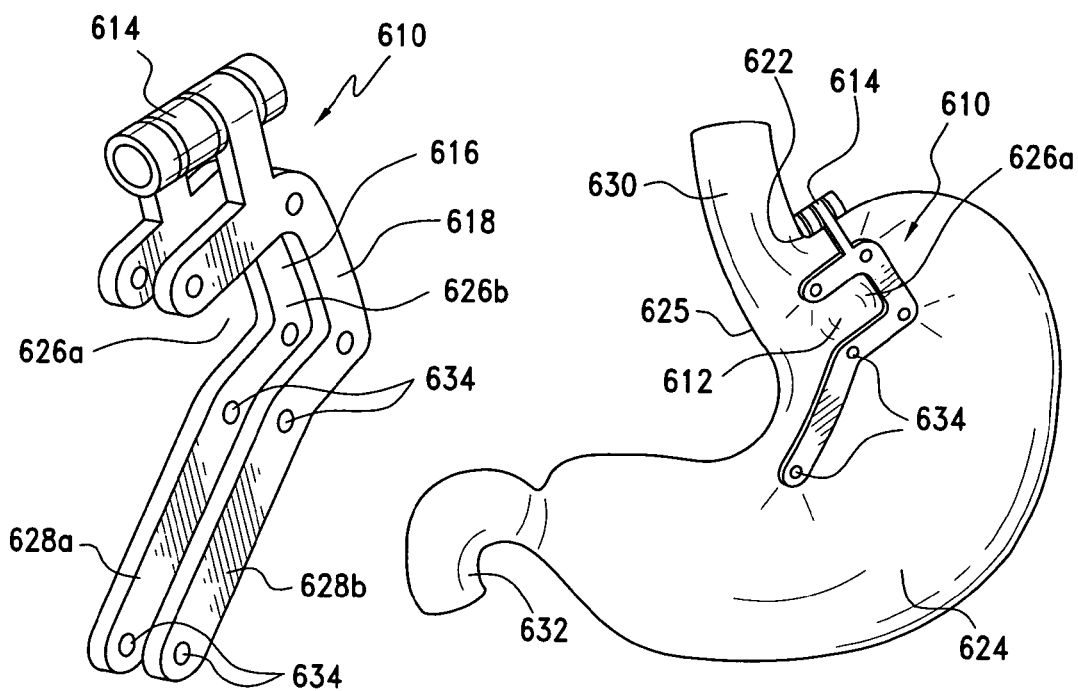
Figures 19, 20:
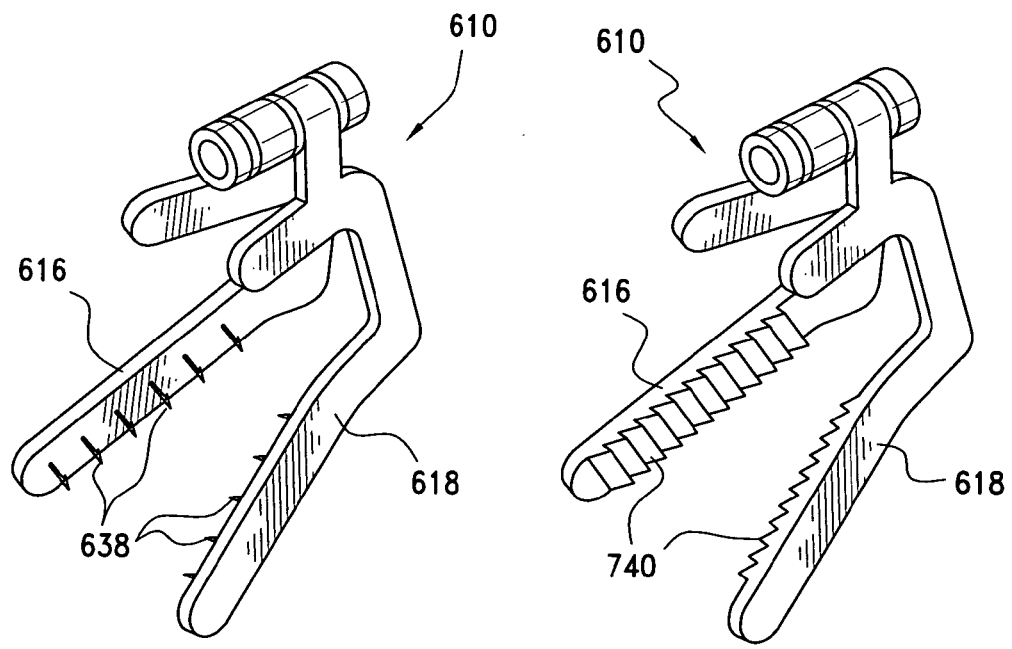

With reference to FIGS. 1 to 26, various embodiments of methods and apparatuses for gastric reduction surgery are disclosed. Each of the embodiments employs a drop-off clamp to create a gastric pouch with a standard size from approximately 15 cc to 30 cc. In accordance with a preferred embodiment of the present invention, most of the clamps are applied transesophageally in a manner creating a limited passageway for food and liquids passing through the stomach.

However, it is contemplated that hybrid approaches employing both transesophageal/laparoscopic techniques and completely laparoscopic approaches may be employed without departing from the spirit of the present invention.

With regard to those embodiments where the clamps are applied to the external surface of the stomach, it is further contemplated the clamps in accordance with the present invention may be presented and deployed in a transgastric approach where the device is inserted transesophageal, a puncture is made outward through the gastric wall, and the clamp is deployed to create the gastric pouch.

In accordance with a first embodiment of the present invention, and with reference to FIGS. 1 to 4, a "bulldog clamp" 10 of a predefined shape is utilized in creating a reduced size gastric pouch 12. As those skilled in the art will appreciate, a bulldog clamp 10 generally includes a clamp body 14 with resiliently coupled first and second arms 16, 18. Each of the first and second arms 16, 18 includes a clamping jaw 20, 22 at a distal end thereof. The clamping jaws 20, 22 of the first and second arms 16, 18 are opposed for clamping about the stomach 24 while the first and second arms 16, 18 are shaped and dimensioned for positioning about the clamped portion of the stomach 24.

The clamping jaws 20, 22 are biased closed in their normal rest position. The clamping jaws 20, 22 are opened for clamping about the stomach 24 when the clamp 10 is gripped along the opposed gripping arms 26, 28 and the gripping arms 26, 28 are drawn together in a manner pulling the clamping jaws 20, 22 apart. After application of the clamp 10 to the exterior surface of the stomach 24, it is contemplated the gripping arms 26, 28 may be removed.

In an effort to create a desirable pouch shape upon the application of the bulldog clamp 10, and in accordance with a preferred embodiment of the present invention, the first and second arms 16, 18 are semicircular and are connected at their respective proximal ends. In this way, the bulldog clamp 10 is substantially circular in cross-section. While a substantially circular cross-sectional shape is employed in accordance with a preferred embodiment of the present invention, those skilled in the art will appreciate the shape may be varied to suit specific needs without departing from the spirit of the present invention.

With regard to the longitudinal shape of the bulldog clamp 10, it is shaped and dimensioned to generally follow the lesser curvature 25 of the stomach 24 as it extends from the esophagus 30 to the pylorus 32. Those skilled in the art will appreciate the exact shape of the bulldog clamp may be varied along the length of the stomach to create pouches of various shapes and sizes without departing from the spirit of the present invention.

The bulldog clamp 10 in accordance with this embodiment is secured along the external surface of the stomach 24. The clamping jaws 20, 22 reach toward the center of the stomach 24 and press the anterior and posterior stomach walls 34, 36 together. With this in mind, it is contemplated the device may also have a barb that penetrates the gastric wall. As such, a pouch 12 of a predefined size is created between the joined anterior and posterior stomach walls 34, 36 and the lesser curvature 25 of the stomach 24 along the curved portion of the stomach 24 extending between the esophagus 30 and the pylorus 32.

The resulting structure of the stomach pouch 12 is that of a tubular member. The tubular member may extend the full length between the esophagus 30 and the pylorus 32 or extend only a portion of the distance from the esophagus 30 to the pylorus 32. Regardless of the length of the tubular member, the gastric remnant allows gastric acid to pass into the food stream. This produces a smaller functional stomach volume as well as a restrictive means for the bolus.

With reference to FIGS. 5, 6, 7 and 8, an alternate embodiment of a clamp 110 for creating a gastric pouch 112 in accordance with the present invention is disclosed. In accordance with this embodiment, a series of C-shaped clamps 110 are positioned within the stomach 124 to create a predefined gastric pouch 112, which reduces the effective size of the individual's stomach 124.

Referring to FIG. 5, the C-shaped clamp 110 is a generally elongated clamp formed with a C-shaped cross-sectional configuration. The C-shaped clamp 110 further includes first, second and third outwardly facing projections 114, 116, 118. The first, second and third outwardly facing projections 114, 116, 118 are positioned circumferentially about the C-shaped clamp 110. As will be described below in greater detail, the outwardly facing projections 114, 116, 118 are adapted for attachment to stomach tissue in a manner securing the tissue to the outer surface 120 of the C-shaped clamp 110 for defining the predetermined gastric pouch shape.

In practice, a series of the C-shaped clamps 110 is placed within the stomach 124 along the lesser curvature of the stomach 124. A vacuum is then applied endolumenally to the inside of the stomach 124. The application of the vacuum brings the anterior and posterior walls 134, 136 of the stomach 124 together. The force of the anterior and posterior walls 134, 136 has the effect of drawing the outwardly facing projections 114, 116, 118 of the C-shaped clamp 110 into the layers of the stomach 120 along the anterior and posterior walls 134,-136 of the stomach 124.

Each of the outwardly facing projections 114, 116, 118 has small, reverse one-way barbs 122 formed along their length. The barbs 122 are designed to engage the stomach tissue forced upon the outwardly facing projections 114, 116, 118 and prevent the tissue from sliding off the outwardly facing projections 114, 116, 118. The depth to which the tissue is penetrated by the outwardly facing projections 114, 116, 118 is controlled by the height of the outwardly facing projections 114, 116, 118 so the surgeon can deploy the C-shaped clamp 110 into the desired layer of tissue.

By positioning a series of C-shaped clamps 110 along the lesser curvature 125 of the stomach 124 between the esophagus 130 and the pylorus 132, and actuating the clamp, the anterior and posterior gastric walls 134, 136 are drawn together adjacent the open end 138 of the C-shaped clamp 110. This creates a restrictive pouch 112 between the joining point of the anterior and posterior gastric walls 134, 136 and the stomach wall along the lesser curvature 125 of the stomach 124. The reduced size stomach pouch 112 enables weight loss for the patient in the same manner as other stomach reduction techniques. Varying the circumference of the C-shaped clamp 110 applied within the patient's stomach 124 may readily vary the size of the restricted pouch.

The resulting structure of the stomach pouch 112 is that of a tubular member. The tubular member may extend the full length between the esophagus 130 and the pylorus 132 or extend only a portion of the distance from the esophagus 130 to the pylorus 132. Regardless of the length of the tubular member, the gastric remnant allows gastric acid to pass into the food stream. This produces a smaller stomach volume as well as a restrictive means for the bolus.

The embodiment disclosed above may be varied such that the C-shaped clamp 210 is adapted for closure by securing the stomach tissue within the C-shaped clamp 210 (see FIGS. 9 and 10). In accordance with this embodiment, the projections 214, 216 are inwardly facing and the stomach tissue is drawn upon the projections 214, 216 by the application of a vacuum. The projections 214, 216 penetrate the tissue and retain it like a fishhook.

Referring to FIGS. 11 and 12, a further embodiment is disclosed. This embodiment employs a girdle clamp 310 for pouch 312 creation. The girdle clamp 310 in accordance with the preferred embodiment, is formed from medical grade wire in the general shape of a tubular scaffolding structure. With this in mind, the girdle clamp 310 includes a resilient first semicircular member 314 and a resilient second semicircular member 316. First and second struts 318, 320 connect the first and second semicircular members 314, 316. The first and second struts 318, 320 are positioned to couple the first and second semicircular members 314, 316 in alignment for positioning along the exterior surface of the stomach 324 in a manner defining a reduced volume pouch 312.

Improved adhesion of the girdle clamp 310 to the stomach 324 is achieved by providing the first and second struts 318, 320 with inwardly facing attachment members 322. For example, burs, teeth, needles, etc., may be formed along the first and second struts 318, 320 for engagement with the stomach wall 324 as the girdle clamp 310 is positioned thereabout. Although various attachment members are disclosed in accordance with a preferred embodiment of the present, other attachment structures known to those skilled in the art may be used without departing from the spirit of the present invention.

The girdle clamp 310 is utilized by positioning the same along the outer surface of the stomach 324 on the lesser curvature 325 of the stomach 324 between the esophagus 330 and pylorus 332. The open ends 338, 340 of the respective first and second semicircular members 314, 316 extend toward the central portion of the stomach 324. The resilient spring bias of the first and second semicircular members 314, 316 draws the first and second struts 318, 320 toward each other in a manner drawing the anterior and posterior stomach walls 334, 336 together along the length of the girdle clamp 310. A series of girdle clamps 310 are secured along this length in a manner defining an extended pouch 312 that extends between the esophagus 330 and the pylorus 332.

The resulting structure of the stomach pouch 312 is that of a tubular member in the shape of the girdle clamp 310. The tubular member may extend the full length between the esophagus 330 and the pylorus 332 or extend only a portion of the distance from the esophagus 330 to the pylorus 332. Regardless of the length of the tubular member, the gastric remnant allows gastric acid to pass into the food stream. This produces a smaller stomach volume as well as a restrictive means for the bolus.

In accordance with an alternate embodiment, and considering that multiple girdle clamps 410 may be utilized in creating a pouch 412 along the stomach 424, the girdle clamps 410 are provided with clips 442 along adjacent semicircular members 414, 416 for securing adjacent girdle clamps 410 along the length of the stomach 424 (see FIGS. 13 and 14). The clips 442 allow for the coupling of adjacent girdle clamps 410 in a convenient manner. While clips 442 are disclosed in accordance with a preferred embodiment, snaps, magnets or other coupling structures could be utilized without departing from the spirit of the present invention.

Referring to FIGS. 15 and 16, a further clamp 510 for use in accordance with the present invention is disclosed. This clamp 510 employs first and second circular spring-biased rings 514, 516. Each ring 514, 516 includes a first end 518a, 518b and a second end 520a, 520b. The first end 518a, 518b and the second end 520a, 520b are in opposed facing relation and are closed to form a complete circle when the ring 514, 516 is unbiased. The first ends 518a, 518b of the respective rings 514, 516 are coupled via a flat clamp member 522 and the second ends 520a, 520b of the respective rings 514, 516 are connected with a second flat clamp member 526. As such, when the first and second rings 514, 516 are unbiased, the clamp members 522, 526 are brought together in a manner compressing an article (for example, stomach tissue) placed therebetween.

As such, and in accordance with this embodiment, the clamp 510 is applied laparoscopically/transgastrically. The clamp 510 is placed over the exterior surface of the stomach 524 along the lesser curvature 525 of the stomach 524 extending between the esophagus 530 and the pylorus 532. The clamp 510 is wrapped about the stomach 524 such that respective circular portion 528a, 528b of the rings 514, 516 aligns with the esophagus 530. The clamp members 522, 526 press down upon an inner portion of the stomach 524 to define the reduced pouch section 512.

As with the embodiment with reference to FIGS. 11 and 12, the first and second clamp members 522, 526 may be provided with texture, barbs, hooks, steeled Velcro, adhesive, sealants, etc., to securely hold the clamp 510 along the exterior surface of the stomach 524. However, other attachment structures known to those skilled in the art may certainly be used without departing from the spirit of the present invention. It is further contemplated the flat clamping members may be curved or otherwise shaped to modify the gastric pouch created by the present clamp.

The resulting structure of the stomach pouch 512 is that of a tubular member substantially conforming to the shape of the clamp 510. The tubular member may extend the full length between the esophagus 530 and the pylorus 532 or extend only a portion of the distance from the esophagus 530 to the pylorus 532. Regardless of the length of the tubular member, the gastric remnant allows gastric acid to pass into the food stream. This produces a smaller stomach volume as well as a restrictive means for the bolus.

A further embodiment in accordance with the present invention is disclosed with reference to FIGS. 17 to 22. This embodiment employs a spring-biased clamp 610 for the creation of a predefined gastric pouch 612. The clamp 610 includes a spring-biased member 614 from which first and second clamp arms 616, 618 depend. The first and second clamp arms 616, 618 are pivotally mounted to the spring-biased member 614 for movement away from each other in a manner permitting placement of stomach tissue therebetween. Each clamp arm 616, 618 includes a pouch cutout 626a, 626b and an extending straight tip 628a, 628b. As those skilled in the art will appreciate, the exact shape of the clamp arm may be varied to define a predetermined pouch shape.

In practice, the spring-biased member 620 is positioned along the exterior surface of the stomach 624 adjacent the angle of Hiss 622 at the entry point of the esophagus 630 to the stomach 624. The clamp arms 616, 618 extend downwardly therefrom along the lesser curvature 625 of the stomach defining a pouch extending toward the pylorus 632.

Secure attachment of the clamp arms 616, 618 to the exterior surface of the stomach 624 may be achieved by the utilization of magnets 634 (see FIG. 17), barbs 638 (see FIG. 19), security teeth 740 (see FIG. 20), one-way latch structure 642 (see FIG. 21), one-way snap structure 644 (see FIG. 22) and/or other structures positioned along the inner surface of the clamping arms 616, 618.

The resulting structure of the stomach pouch 612 is that of a tubular member conforming to the shape of pouch cutout 626a, 626b and the straight arms 628a, 628b. The tubular member may extend the full length between the esophagus 630 and the pylorus 632 or extend only a portion of the distance from the esophagus 630 to the pylorus 632. Regardless of the length of the tubular member, the gastric remnant allows gastric acid to pass into the food stream. This produces a smaller stomach volume as well as a restrictive means for the bolus.

In accordance with yet a further embodiment, the clamp disclosed above with reference to FIGS. 23 and 24, may be varied by providing for replacement of the straight tips 734 at the distal end 736 of the first and second clamping arms 716, 718. In particular, release buttons 738 or dovetail connections 739 may be provided such that that the straight tips 734 at the distal end 736 of the first and second clamping arms 716, 718 can be removed and replaced with tips of different shapes, lengths and/or securing structures.

A further clamp embodiment 810 adapted for use during RYGB procedures is disclosed with reference to FIGS. 25 and 26. This embodiment employs a spring-biased clamp 810 for the creation of a predefined gastric pouch 812. However, the pouch 812 is inverted, separating the entry point from the esophagus 830 from the remainder of the stomach 824.

The clamp 810 includes a spring-biased member 814 from which first and second clamp arms 816, 818 depend. The clamp arms 816, 818 are pivotally mounted to the spring-biased member 814 for movement away from each other in a manner permitting placement of stomach tissue therebetween. Each clamp arm 816, 818 includes a pivotal central hinge 820, 822 allowing for adjustment in the size of pouch 812.

In practice, the clamp 810 is applied over the lesser curve 825 of the stomach 824. A gastrotomy may then be performed and a RYGB procedure performed with the clamp 810 taking the place of the staples commonly employed during a RYGB procedure. It is contemplated the clamp arms may be provided with a concave portion adjacent the spring-biased member for defining an opening allowing for digestion while the clamp is in place.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A clamp for gastric reduction surgery, comprising:
a clamp body shaped and dimensioned to create a gastric pouch with a standard size from approximately 15 cc to approximately 30 cc;
wherein the clamp body is generally elongated with a C-shaped cross-section and includes at least one outwardly facing projection, the at least one outwardly facing projection includes reverse, one-way barbs to engage stomach tissue and prevent the stomach tissue from sliding off the at least one outwardly facing projection.

2. The clamp according to claim 1, wherein the clamp body is generally elongated with a C-shaped cross-section and includes first, second and third outwardly facing projections, and the first, second and third outwardly facing projections are positioned circumferentially about the clamp body.

3. A clamp for gastric reduction surgery, comprising:
a clamp body shaped and dimensioned to create a gastric pouch with a standard size from approximately 15 cc to approximately 30 cc;
wherein the clamp body includes a spring-biased member from which a first clamp arm and a second clamp arm depend, the first clamp arm and the second clamp arm are pivotally mounted to the spring-biased member for movement away from each other in a manner permitting placement of stomach tissue therebetween, and each of the first clamp arm and the second clamp arm includes a pivotal central hinge allowing for adjustment in the size of pouch.

* * * * *